United States Patent [19]

McCann et al.

[11] Patent Number: 5,494,797
[45] Date of Patent: Feb. 27, 1996

[54] METHOD FOR DETECTING LYME DISEASE

[75] Inventors: Daisy S. McCann, Ontario, Canada; Paul Chuba, Detroit, Mich.

[73] Assignee: McCann Associates, Inc., Wayne, Mich.

[21] Appl. No.: 272,274

[22] Filed: Jul. 8, 1994

Related U.S. Application Data

[63] Continuation of Ser. No. 743,132, Aug. 9, 1991, abandoned.

[51] Int. Cl.$^6$ ....................................................... C12Q 1/68
[52] U.S. Cl. .................................. 435/6; 935/77; 935/78
[58] Field of Search ............................... 435/6; 536/24.32

[56] References Cited

U.S. PATENT DOCUMENTS

| | | | |
|---|---|---|---|
| 4,358,535 | 11/1982 | Falkow et al. | 435/5 |
| 4,563,417 | 1/1986 | Albarella et al. | 435/6 |
| 4,656,127 | 4/1987 | Mundy | 435/6 |
| 4,705,886 | 11/1987 | Levenson et al. | 560/159 |
| 4,717,653 | 1/1988 | Webster, Jr. | 435/5 |
| 4,721,617 | 1/1988 | Johnson | 424/92 |
| 4,743,535 | 5/1988 | Carrico | 435/6 |
| 4,808,519 | 2/1989 | Hartley et al. | 435/6 |
| 4,851,330 | 7/1989 | Kohne | 435/6 |
| 4,868,105 | 9/1989 | Urdea et al. | 435/6 |
| 4,883,750 | 11/1989 | Whiteley et al. | 435/6 |
| 4,888,276 | 12/1989 | Shelburne | 435/7 |
| 4,968,602 | 11/1990 | Dattagupta | 435/6 |
| 5,279,938 | 1/1994 | Rosa | 435/6 |
| 5,401,631 | 3/1995 | Lane et al. | 435/6 |

FOREIGN PATENT DOCUMENTS

| | | | |
|---|---|---|---|
| 0164586 | 12/1985 | European Pat. Off. | C12Q 1/68 |
| 0421725 | 4/1991 | European Pat. Off. | |
| WO9106676 | 5/1991 | WIPO | C12Q 1/68 |
| WO9114002 | 9/1991 | WIPO | C12Q 1/68 |
| WO9119814 | 12/1991 | WIPO | C12Q 1/68 |

OTHER PUBLICATIONS

Storti et al. Sequence Homology Between Mitochondrial DNA and Nuclear DNA in the Yeast, Saccharomyces cerevisiae, Biochemistry (1974) 13:4447–4455.

Matthews et al, Review: Analytical Strategies for the Use of DNA Probes, Anal. Biochem (1988) 169:1–25.

Dialog Information Services, File 154: Medline 66–92/May, accession No. 07580973, Medline accession No. 91099973, Goodman J. L. et al: "Molecular detection of persistent Borrelia burdorferi in the urine of patients with active Lyme disease", *Infect. Immun.* Jan. 1991, 59 (1) pp. 269–278 (Abstract).

D. W. Dorward, T. G. Schwan and C. F. Garon (Jun. 1991), Immune Capture and Detection . . . Humans, J. Clin. Microbiol., vol. 29(6):1162–1170.

J. L. Goodman, P. Jurkovich, C. Kodner, and R. C. Johnson, Persistent Cardiac . . . Hamsters, J. Clin. Microbiol., (May 1991), vol. 29(5):894–896.

J. Piesman, G. O. Maupin, E. G. Campos, and C. M. Happ, Duration of Adult . . . Isolation Method, J. Infect. Disea., (Apr. 1991), vol. 163:895–897.

A. M. Lebech, P. Hindersson, J. Vuust, and K. Hansen, Comparison of In Vitro Culture . . . Animals, (Apr. 1991), J. Clin. Microbiol., vol. 29(4):731–737.

E. Aberer and P. H. Duray, Morphology of Borrelia . . . Staining Methods, J. Clin. Microbiol., (Apr. 1991), vol. 29(4)764–772.

P. A. Rosa, D. Hogan, and T. G. Schwan, Polymerase Chain Reaction . . . burgdorferi, J. Clin. Microbiol., (Mar. 1991), vol. 29(3):524–532.

C. S. Pavia, V. Kissel, S. Bittker, F. Cabello, and S. Levine, Antiborrelial . . . Spirochete, J. Infect. Disea., (Concise Commun.), (Mar. 1991), vol. 163:565–659.

S. M. Callister, J. A. Nelson, R. F. Shell, D. A. Jobe, R. Bautz, W. A. Agger, and J. Coggins, Survey . . . Illinois, J. Clin. Microbiol, (Feb. 1991), (Feb. 1991), vol. 29(2):403–406.

W. J. Simpson, W. Burgdorfer, M. E. Schrumph, R. H. Karstens, and T. G. Schwan, Antibody . . . Animals, J. Clin. Microbiol., (Feb. 1991), vol. 29(2):236–243.

C. Collins and G. Peltz, Immunoreactive Epitopes on an Expressed Recombinant . . . burgdorferi, Infect. Immun., (Feb. 1991), 59(2):514–520.

Y. Ma, A. Sturrock, and J. J. Weis, Intracellular Localization . . . Endothelial Cells, Infect. Immun., (Feb. 1991), vol. 59(2):671–678.

G. S. Gassmann, E. Jacobs, R. Deutzmann, and U. B. Göbel, Analysis of the Borrelia burgdorferi . . . Product, J. Bacteriol., (Feb. 1991), vol. 173(4):1452–1459.

K. Georgilis, A. C. Steere, and M. S. Klempner, Infectivity of Borrelia . . . Phagocytic Cells, J. Infect. Disea., (Jan. 1991), vol. 163:150–155.

R. T. Greene, D. A. Hirsch, P. L. Rottman, and T. M. Gerig, Interlaboratory . . . Canine Sera, J. Clin. Microbiol., (Jan. 1991), vol. 29(1):16–20.

L. Zöller, S. Burkard, and H. Schäfer, Validity of Western Immunoblot Band . . . Lyme Borreliosis, J. Clin. Microbiol., (Jan. 1991), vol. 29(1):174–182.

K. Hansen, K. Pil, and A. M. Lebech, Improved Immunoglobulin M Serodiagnosis . . . burgdorferi Flagella, J. Clin. Microbiol., (Jan. 1991), vol. 29(1):166–173.

J. F. Anderson, S. W. Barthold, and L. A. Magnarelli, Infectious but Nonpathogenic . . . burgdorferi, J. Clin. Microbiol., (Dec. 1990), vol. 28(12):2693–2699.

D. H. Persing, S. R. Telford III, P. N. Rys, D. E. Dodge, T. J. White, et al., Detection . . . Ticks, Science, (Sep. 1990), (List continued on next page.)

*Primary Examiner*—Stephanie W. Zitomer
*Attorney, Agent, or Firm*—Reising, Ethington, Barnard & Perry

[57] ABSTRACT

Described is a method of detecting the presence of Lyme Disease organism comprising the steps of (a) combining a sample with an oligonucleotide probe for the organism; (b) hybridizing the probe with the organism; and (c) determining the presence of the organism hybridized with the probe. Also described is a kit containing a hybridization buffer, a labeled probe, and filter assemblies on which the hybridized product may be placed during the hybridization reaction. The kit may also contain positive and negative control filters to assist in the evaluation of unknown specimens.

10 Claims, 1 Drawing Sheet

OTHER PUBLICATIONS vol. 249:1420–1423.

S. W. Barthold, D. S. Beck, G. M. Hansen, G. A. Terwilliger, and K. D. Moody, Lyme Borreliosis . . . Laboratory Mice, J. Infect. Disea., (Jul. 1990), vol. 162:133–138.

R. B. Lefebvre, G. C. Perng, and R. C. Johnson, The 83–Kilodalton Antigen . . . Chromosomal Gene, J. Clin. Microbiol., (Jul. 1990), vol. 28(7):1673–1675.

D. C. Malloy, R. K. Nauman, and H. Paxton, Detection of Borrelia burgdorferi . . . Chain Reaction, J. Clin. Microbiol., (Jun. 1990), vol. 28(6):1089–1093.

A. C. Steere, V. P. Berardi, K. E. Weeks, E. L. Logigian, and R. Ackermann, Evaluation . . . Neuroborreliosis, J. Infect. Disea., (Jun. 1990), vol. 161:1203–1209.

S. Kurashige, M. Bissett, and L. Oshiro, Characterication of a Tick Isolate . . . Surface Protein, J. Clin. Microbiol., (Jun. 1990), vol. 28(6):1362–1366.

J. C. Garcia–Monco, B. F. Villar, J. C. Alen, and J. L. Benach, Borrelia . . . Early Invasion, J. Infect. Disea., (Jun. 1990), vol. 161:1187–1193.

K. Hansen, M. Cruz, and W. Link, Oligoclonal Borrelia burgdorferi Specific IgG . . . Lyme Neuroborreliosis, J. Infect. Disea., (Jun. 1990), vol. 161:1194–1202.

N. E. Barka, M. S. Agopian, and J. B. Peter, (Correspondence), False–Positive . . . Rheumatoid Factor, J. Infect. Disea., (Jun. 1990), vol. 161:1312.

J. A. Nelson, M. J. Bankowski, B. J. Newton, C. A. Benson, R. Kaplan, et al., (Corres.), Detection . . . Disease, J. Infect. Disea., (May 1990), vol. 161:1034–1035.

J. F. Anderson et al., (Correspondence) Borrelia burgdorferi and Ixodes dammini . . . Philadelphia Area, J. Infect. Disea., (Apr. 1990), vol. 161:811–812.

R. B. LeFebvre, R. S. Lane, G. C. Perng, J. A. Brown, and R. C. Johnson, DNA and Protein . . . California, J. Clin. Microbiol., (Apr. 1990), vol. 28(4):700–707.

D. H. Persing, S. R. Telford III, A. Spielman, and B. W. Barthold, Detection of Borrelia . . . Chain Reaction, J. Clin. Microbiol., (Mar. 1990), vol. 28:566–572.

J. Lindenmyer, M. Weber, J. Bryant, E. Marquez, and A. Onderdonk, Comparison of Indirect . . . in Dogs, J. Clin. Microbiol., (Jan. 1990), vol. 28(1):92–96.

E. Aberer, C. Brunner, G. Suchanek, H. Klade, A. Barbour, G. Stanek and H. Lassman, Molecular . . . Human Tissue, Annals of Neurology, (Dec. 1989), vol. 26(6):732–737.

C. M. Wayand and J. J. Goronzy, Immune Response to Borrelia burgdorferi in Patients with Reactive Arthritis, Arthritis and Rheumatism, (Sep. 1989), vol. 32(9):1057–1064.

Cruachem, Inc., Aminomodifiers and Easy Label Kits User Manual (Spring 1989, Rev. Aug. 1989).

H. Krüger, K. Reuss, M. Pulz, E. Rohrbach, K.–W. Pflughaupt, R. Martin, and H. G. Mertens, Meningoradicultis . . . years, J. Neurol., (Spring 1989), vol. 236:322–328.

T. G. Schwan and A. G. Barbour, Efficacy of Nucleic Acid Hybridization Probes . . . Borrelia burgdorferi, AM. NY Acad. Sci., (1988) 539:419–421.

P. J. Chuba, K. Pelz, G.Krekeler, T. S. De Isele, and U. Göbel, Synthetic . . . Human Periodontitis, J. Gen. Microbiol., (1988), vol. 134:1931–1938.

H. A. White, Oligonucleotide Synthesis, Molecular Biology and Biotechnology, 2nd edition (1988), edited by J. M. Walker and E. B. Gingold, Royal Society of Chemistry.

R. Frank, A. Meyerhans, K. Schwellnus and H. Blocker, Simultaneous Synthesis . . . Complete Methodology, Methods in Enzymology (1987), vol. 154:221–249.

M. H. Caruthers, A. D. Barone, S. L. Beaucag, D. R. Dodds, E. F. Fisher, et al. Chemical . . . Phosphoramidite Method, Methods in Enzymology, (1987), vol. 154:287–313.

S. J. Horvath, J. R. Firca, T. Hunkapiller, M. W. Hunkapiller, and L. Hood, An Automated . . . 3'–Phosphoramidites, Methods in Enzymology, (1987), vol. 154:314–326.

P. K. Horan, S. E. Slezak, and G. Poste, Improved flow . . . immunofluorescence, Proc. Natl., Acad. Sci. USA, (Nov. 1986), 83:8361–8365.

Preparation of RadioLabelled Antigens, Molecular Immunology (1984) edited by Atassi, VanOss, and Absolom, Dekker, pp. 410–411.

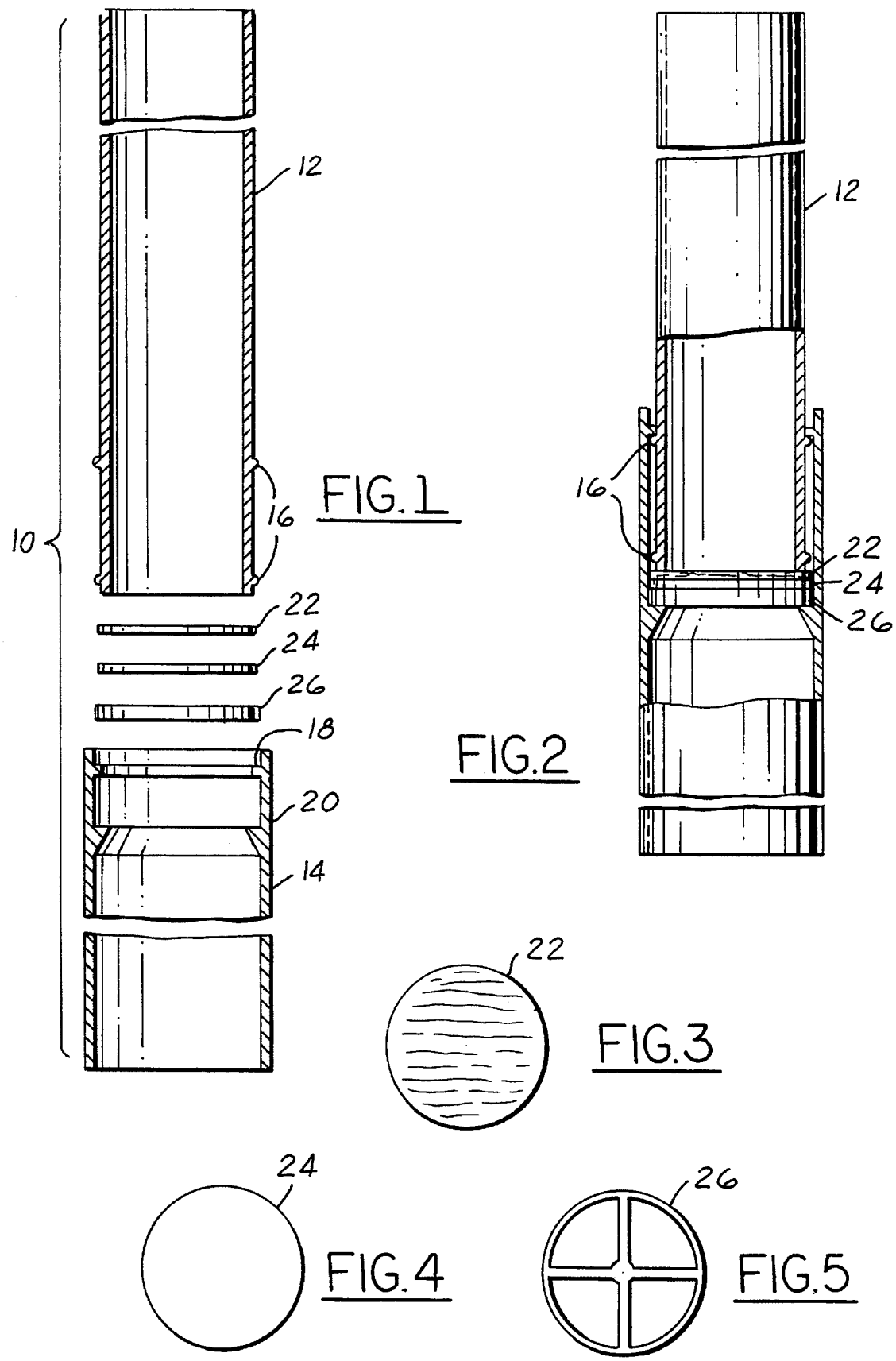

METHOD FOR DETECTING LYME DISEASE

This application is a continuation of Ser. No. 07/743,132 filed Aug. 9, 1991, now abandoned.

TECHNICAL FIELD

This invention relates to Lyme disease.

BACKGROUND ART

Lyme disease is a systemic tick-borne illness generally characterized as a reddish or purplish target rash radiating around the tick bite. Lyme disease is generally characterized as being caused by a spirochete bacteria *Borrelia burgdorferi*. Various sub-species and strains of this organism have been identified, but their inter-relationship is not finally determined.

The diagnostic acumen for Lyme Disease is poor. The ability to quickly and reliably detect the presence of *Borrelia burgdorferi* in patients suspected of having Lyme Disease is of great medical importance. The in-vitro culture of *Borrelia burgdorferi* is currently the most effective technique but is an impractical method of diagnosis.

A technique for detecting the presence of the organism *Borrelia burgdorferi* by utilizing antibodies specific for at least one antigen of the organism is described in U.S. Pat. No. 4,888,276. The use of other monoclonal and polyclonal antibody tests for detection of *Borrelia burgdorferi* antigens is described in the JOURNAL OF CLINICAL MICROBIOLOGY, June 1991, page 1162–1170. However, immunological methods are neither sufficiently sensitive nor reliable for diagnostic screening.

Molecular biological techniques have also been attempted. PCR (Polymerase Chain Reaction) amplification and subsequent hybridization of amplified material with radiolabeled probe has been reported in the JOURNAL OF CLINICAL MICROBIOLOGY, June 1990, page 1089–1093 and in the JOURNAL OF CLINICAL MICROBIOLOGY, April 1991, page 731–737. However, this PCR work was not done on clinical samples. In general, the PCR technique works best when amplifying nucleic acid materials present in pure culture or in joint or cerebrospinal fluid. The PCR technique has limited utility in whole blood or plasma samples. Therefore, the amplification technique does not provide an adequate diagnostic method for detection of *Borrelia burgdorferi* in individuals suspected of having Lyme Disease.

SUMMARY OF THE INVENTION

The present invention provides a quick and reliable diagnostic technique suitable for use with whole blood or plasma samples taken from patients suspected of having Lyme disease.

The present invention is concerned with a method for detecting the presence of an organism associated with Lyme disease, such as, *B. burgdorferi* comprising the steps:

a). combining a sample with an oligonucleotide probe for the organism;

b). hybridizing the probe with the organism; and c). determining the presence of the organism hybridized with the probe.

It is an object of the present invention to use an oligonucleotide that has the ability to hybridize with the organism in clinical or experimental samples without amplification.

It is also an object of the present invention to describe a oligonucleotide that has the ability to act as a hybridizing probe with the nucleic acids of the organism. The oligonucleotide can be characterized as containing the following formula:

5'NH2 GTT CGC CTT CGC CTC CGG TAT TC (SEQ ID NO: 1) or 5' GTT CGC CTT CGC CTC CGG TAT TC NH₂

BRIEF DESCRIPTION OF THE DRAWINGS

FIG. 1 is an exploded sectional view of the apparatus employed in the Lyme disease detection method;

FIG. 2 is the assembled structure of FIG. 1;

FIG. 3 is a top view of the filter used in the apparatus of FIG. 1;

FIG. 4 is a top view of another filter used in the apparatus of FIG. 1; and

FIG. 5 is a top view of the filter support used in the apparatus of FIG. 1.

DETAILED DESCRIPTION

The term "oligonucleotide" is generally taken to mean oligo-deoxyribonucleotide. Oligonucleotide lengths are usually stated as numbers: e.g., 18 "mer", 35 "mer", etc. Sequences are given using the accepted abbreviations. Correctly, the component nucleotides are abbreviated 'dA' (deoxyadenylate) 'dG' (deoxyguanylate) 'dC' (deoxycytidylate) and 'dT' (deoxythymidylate). In the present application, the most preferred oligonucleotide is as follows:

5' NH2 GTT CGC CTT CGC CTC CGG TAT TC. (SEQ ID NO: 1)

The most preferred is that the oligonucleotide has a primary amine bound to the terminal 5' or 3' phosphoribosyl moiety.

It is to be appreciated that for an oligonucleotide to be a probe for the organism *burgdorferi*, it is not necessary that a 23 "mer" be utilized. It may be that only an effective portion of the aforementioned oligonucleotide need be used. For example, the first nine oligonucleotides or the last nine oligonucleotides or the nine in the middle may be useful. Also, the 23 "mer" oligonucleotide may be a part of a larger sequence of bases and still be functional as a hybridizing agent for *B. burgdorferi*. Therefore, when utilizing the phrase, "oligonucleotide probe" of the present application it includes the 23 "mer" and all effective portions thereof, sufficient to hybridize with *B. burgdorferi* organism.

The 23 "mer" oligonucleotide can be synthesized by any well known technique for oligonucleotide sequences. A number of references describe synthesis of synthetic oligonucleotides such as oligonucleotide synthesis, H. A. White MOLECULAR BIOLOGY AND BIOTECHNOLOGY, edited by Walker, J. M., Gingold, E. B.; ROYAL SOCIETY OF CHEMISTRY, London Chapter 16 pages 349–371. Also, R. Frank et al., *Simultaneous Synthesis and Biological Applications of DNA Fragments: An Efficient and Complete Methodology* METHODS IN ENZYMOLOGY, Volume 154, pages 221–249; M. H. Caruthers et al., *Chemical Synthesis of Deoxyoligonucleotides by the Phosphoramidite Method*, METHODS IN ENZYMOLOGY, Vol. 154, pp. 287–313; S. J. Horvath et al., An *Automated DNA Synthesizer Employing Deoxynucleotide 3'-Phosphoramidites,* METHODS IN ENZYMOLOGY, Vol. 154, pp. 314–326. Commercial machines are likewise available for producing the desired oligonucleotide. Such machines are generally available from Beckman Instruments or Applied Biosystems.

The present application is likewise concerned with a method for detecting the presence of the organism *B. burgdorferi*. The sample that is to be analyzed can be a human sample or animal sample. The sample may be a biological fluid such as blood, plasma, serum, sputum, spinal fluids, tissue extracts, animal fluids, culture medium, urine, and the like. The sample may also be portions of the above biological fluid including blood plasma and the like. The preferred sample is whole blood as extracted from a human or an animal. The test is a non-invasive in-vitro test, but rather is made on a specimen taken from the human or animal.

The mechanism for detecting the presence of the organism is to hybridize the oligonucleotide with the organism. By hybridization is meant a process whereby single-stranded DNA or RNA molecules are combined and double-stranded molecules formed if complementary sequences exist in the specimen to be tested.

To assist in the determination of the product of hybridization, the oligonucleotide probe is marked or treated with a label to facilitate the subsequent detection.

Any number of convenient labels may be placed on the probe. The probe could be radioactively labeled or covalently bonded with other labels such as a fluorescent label or other appropriate label that would make the probe susceptible to detection, such as being bound to an enzyme. The probe could be reacted with an radioactive marker such as $^{125}$I or $^{131}$I or $^{32}$P. Radioactive labels such as $^{3}$H, $^{14}$C and the like may also be used. The most preferred technique is radiolabeling with $^{125}$I which, because of its half-life, is the most practical for use in a clinical setting.

A radioactive iodine conjugate may be reacted with the oligonucleotide using standard techniques, heretofore used in the biochemical arts to label protein. Specifically, the probe bearing a 5' or 3' primary amine could be reacted with Bolton Hunter (BH) reagent followed by a borate solution. See Preparation of Radiolabelled Antigens MOLECULAR IMMUNOLOGY, (1984) edited by Atassi, VanOss, and Absolom, Dekker, 1984, pages 410–411. The labeled probe could be subsequently purified on a BioRad spin column followed by final purification on polyacrylamide gel or by reverse phase High Performance Liquid Chromatography (HPLC).

The oligonucleotide probe could also be reacted with the fluorescing agent such as fluorescein isothiocyanate (FITC), tetramethylrhodamine isothiocyanate (TRITAC), texas red, phycoerythrin (PE), allophycocyanin (APC), and the like. For varying lengths of the nucleotide probe, different reagents could be utilized and therefore detected in a fluorometer or in a multicolor fluorescent system by using a flow cytometer, NATIONAL ACADEMY OF SCIENCES U.S.A., Volume 83, pages 8361–8365, November 1986.

If an Elisa technique were to be utilized, then the nucleotide probe could be reacted with an enzyme which enzyme could then be detected as in a commercially available enzyme linked immunosorbent assay. Suitable enzymes may be horse radish peroxidase, alkaline phosphatase, urease, and the like. Commercially available Elisa are readily available.

Other markers may likewise be used such as chemiluminescers such as luciferin, 2,3-dihydrophthalazinediones, e.g., luminol, and the like.

After the appropriately labeled probe is prepared, it can then be hybridized with the specimen. The nucleic acid material is placed in contact with a physical support on which the denatured nucleic acids adhere. In general, the *Borrelia burgdorferi* spirochetes or vesicles containing nucleic acid material shed by *Borrelia burgdorferi* contained in the specimen will be lysed and their nucleic acids denatured in the presence of heat and hybridization buffer. Thereafter, the labeled probe is contacted with the nucleic acid material and incubated. Subsequently, the support on which the hybridization reaction has taken place can then be utilized to detect the presence of the hybridized product.

Most preferably, the solid support on which the nucleic acids are immobilized is a nitrocellulose filter resting on a blotter filter and filter support as contained within the plastic tube of the diagnostic unit described below. Any nonbrittle plastic to which sample materials and reagents will not adhere, such as polypropylene, may be used.

Number 10 of FIG. 1 consists of the components comprising the preferred diagnostic unit to be employed in the detection of *Borrelia burgdorferi* from clinical samples of whole blood or plasma.

FIG. 2 shows the components assembled and ready to accept a diagnostic sample. Specifically, a cylindrical plastic upper chamber 12, having a height of 7 centimeters and an outer diameter of 0.98 centimeters bears exteriorly protruding snap-lock connectors 16 separated by a vertical distance of 0.9 centimeters. A plastic lower chamber 14, having a height of 4 centimeters and an inner diameter of 1.00 centimeters contains an interiorly protruding snap-lock connector 18 and a ridge 20 separated by a vertical distance of 1.0 centimeters. A plastic filter support 26 of 0.1 centimeter thickness rests on the ridge 20 of lower chamber 14. On the filter support 26 rests filter paper 24, such as Whatman No. 3 quality. Above filter paper 24 rests 22 which is a filter, such as nitrocellulose, nylon, or other suitable hybridization materials, on which nucleic acid material is retained for hybridization with labeled probe. Filters 24 and 22 have an outer diameter of 0.97 centimeters. The filter support 26 and filters 22 and 24 are to be placed within the lower chamber 14 as the first step in assembly of the diagnostic unit 10. Next, the lower portion of upper chamber 12 is placed into the upper portion of lower chamber 14 such that the lower snap-lock connector 16 rests upon ridge 20 and the upper snap-lock connector 16 fits securely immediately below snap-lock connector 18. The snap-lock connection serves to hold the sandwich of filter support 26 and filters 24 and 22 securely in place, such that the entire blood sample is passed through the filters 24 and 22.

FIG. 3 is a top view of 22 which is a filter of nitrocellulose or other suitable material on which nucleic acid material is retained for hybridization with the labeled probe.

FIG. 4 is a top view of 24 and is filter paper, such as Whatman No. 3 quality, which, being located below the filter 22 of FIG. 3, serves to draw away excess fluid from the filter 22.

FIG. 5 is a top view of the plastic support unit 26 which functions to hold the filters in place in the assembled diagnostic unit 10, as shown in FIG. 2.

It is to be appreciated that any technique for permitting the contact of the hybridization product would be satisfactory. While a physical support such as a nitrocellulose filter may be utilized, obviously, other physical medium may likewise be used such as a coated tube, resin beads, a sandwich assay technique, a plastic strip, a microtiter well, and the like.

It may also be desired to vary how the detection could take place depending upon the label that would be utilized.

In the most preferred embodiment, the hybridization fluid that is utilized is a buffer of Denhardt's solution and of saline citrate medium further containing sodium dodecylsulfate together with salmon sperm DNA. The latter acts as a medium to prevent interference by non-specific DNA binding.

Due to the uniqueness of the technique as described herein, the present invention is also concerned with a Lyme disease kit which contains a hybridization buffer, the labeled probe, and filter assemblies on which the hybridized product may be placed during the hybridization reaction. The kit may also contain positive and negative control filters to assist in the evaluation of unknown specimens.

Having described the invention, listed below are preferred embodiments wherein all temperatures are in degrees Centigrade and all parts are parts by weight, unless otherwise indicated.

EXAMPLE 1

A diagnostic unit made of polypropylene and containing filters, which is substantially comparable to that described in FIG. 1, is placed in a centrifuge tube. Fresh human EDTA (ethylene diamine tetraacetic acid) plasma is placed in the unit in the amount of 2.0 ml and centrifuged for 10 minutes. Centrifugation causes the material to pass through the filter assembly within the diagnostic unit. Nucleic acid material is retained on filter 22 and the effluent is captured for disposal in the centrifuge tube. The two components of the diagnostic unit are then separated and the nitrocellulose filter is transferred to an appropriately labeled second nonadherent plastic tube suitable for use in a gamma counter. The tube is then heated for 30 minutes at 80° Centigrade. A warm hybridization buffer at 65° Centigrade in the amount 500 µl (microliter) is added to the specimen tube as well as the positive and negative control tubes. The material is incubated for two hours at 65° Centigrade in a shaking water bath. Thereafter, 25 microliters of the iodinated probe is added to each specimen and the material is then incubated for two hours at 65° Centigrade. Thereafter, the buffer is decanted, washed with one milliliter of a wash solution, shaken for five minutes and then decanted. The filters are then counted in a gamma counter. Thereafter, one can determine from the positive and negative controls and the active specimen the presence of the $B.$ $burgdorferi$ organism.

The procedure was followed and found to have an 89% clinical sensitivity and 94% clinical specificity as indicated by the following result of a blind study of 45 donor samples. Twenty-seven of the 45 samples were taken from people clinically judged to be positive for Lyme Disease based on 2 or more criteria accepted as diagnostic for Lyme Disease. These criteria include tick bite, musculo-skeletal involvement, cardiac involvement, neurological involvement, flu, or positive in-vitro culture of $Borrelia$ $burgdorferi$. The other 18 donors were clinically judged to be negative for Lyme Disease. Of the 27 Lyme Disease positive donors, 24 were positive in the gene probe assay of the present invention and 3 were negative. Of the Lyme Disease negative donors, 17 were judged negative and 1 positive. Positive and negative gene probe results were based upon cpm (counts per minute) scoring as compared to positive and negative controlled samples as illustrated in Table 1.

TABLE 1

| Specimen | CPM | Scoring |
| --- | --- | --- |
| Control 1 (neg) | 512 | |
| Control 2 (neg) | 459 | |
| 135 | 532 | − |
| 138 | 21391 | + + |
| 139 | 1690 | + + |

TABLE 1-continued

| Specimen | CPM | Scoring |
| --- | --- | --- |
| 140 | 3032 | + + |
| 141 | 578 | − |
| 142 | 3767 | + + |
| 144 | 850 | + + |
| 145 | 2209 | + + |
| 147 | 1039 | + + |
| 148 | 13596 | + + |
| 149 | 1993 | + + |
| 151 | 865 | + + |
| Control 3 (pos) | 6938 | |
| Control 4 (pos) | 4057 | |

The solutions that were utilized in the above experiment are described as follows. The hybridization buffer is prepared by blending the following materials to make 100 ml:

Hybridization Buffer per 100 ml 5 ml of 100× (fold) Denhardt's solution 25 ml of 20× Standard Saline Citrate 200 µl sodium dodecylsulfate solution 10 ml salmon sperm DNA solution bring to 100 ml after adjusting to pH 8.0

The Denhardt's solution is made from the following solution:

100× Denhardt's Solution (500 ml) 10 g Ficoll 400 10 g polyvinylpyrrolidone 10 g bovine serum albumin (Fraction V) bring to 500 ml (can be stored frozen)

The standard saline citrate solution is prepared from the following materials:

20× Standard Saline Citrate (11) 175 g sodium chloride 88 g trisodium citrate dissolve in 500 ml water adjust to pH 7.0 with 1 MCH1 bring to 1000 ml The sodium dodecylsulfate solution is prepared as follows:

Sodium dodecylsulfate solution (SDS) 5 mg SDS/ml Tris-EDTA buffer Tris-EDTA buffer pH 8.0 10 mM Tris-Cl pH 8.0 1 mM EDTA pH 9.0

The salmon sperm DNA solution is prepared as follows:

Salmon Sperm DNA solution Dilute 1 ml Tris EDTA buffer to 100 ml with deionized water add—100 mg salmon sperm to 100 ml of water diluted Tris EDTA buffer The probe is prepared by iodinating the 23 "mer" as follows:

To 250 µg probe add 50 µl of deionized water.

Dry 500 µCi of Bolton Hunter reagent (BH) in its reaction vessel under a slow stream of nitrogen in an appropriate hood and behind a lead glass shield. To the reaction vessel add 45 µl of probe solution, followed by 4.5 µl of 1M borate (final borate concentration 0.1M) mix and incubate for 30 minutes.

Set 1 µl of reaction mixture aside for counting and run the balance of the mixture through a Bio Rad spin column.

Take 1 µl of the purified probe and count it and the 1 µl of reaction mixture set aside before purification. Radioactive incorporation in the probe should be 40% to 50%.

Final purification of probe is performed on polyacrylamide gel (20%) or on reverse phase HPLC.

To detect the presence of $B.$ $burgdorferi$, a culture strain was obtained from American Type Culture Collection (ATCC 35 210) from which the positive controls were prepared.

While the forms of the invention herein disclosed constitute presently preferred embodiments, many others are possible. It is not intended herein to mention all of the possible equivalent forms or ramifications of the invention. It is

What is claimed is:

1. A method of detecting the presence of Lyme disease by detecting the organism *Borrelia burgdorferi* associated with Lyme disease comprising the steps of;
    (a) combining a sample suspected to contain the organism *Borrelia burgdorferi* with an oligonucleotide probe for the nucleic acid of the organism having the oligonucleotide sequence: GTT CGC CTT CGC CTC CGG TAT TC;
    (b) hybridizing the oligonucleotide probe with the nucleic acid of the organism; and
    (c) determining the presence of Lyme Disease associated with the nucleic acid of the organism hybridized with the probe.

2. The method of claim 1 wherein the probe is labeled with a radioactive label.

3. The method of claim 1 wherein the probe is labeled with a fluorescing agent.

4. The method of claim 1 wherein the probe is labeled with an enzyme.

5. The method of claim 1 wherein the determination of the presence or the organism is performed by the hybridizing of the nucleic acid of the probe on a solid phase.

6. The method of claim 5 wherein the solid phase is filter paper.

7. The method of claim 5 wherein the solid phase is resin particles.

8. The method of claim 1 wherein the probe is:
    5'xGTT-CGC-CTT-CGC-CTC-CGG-TAT-TC wherein X=5' Amine or
    5'GTT-CGC-CTT-CGC-CTC-CGG-TAT-TCX wherein X=3' amine.

9. The method of claim 8 wherein the probe is radioiodinated by reaction of the 3' or 5' primary amine with Bolton Hunter reagent.

10. The method of claim 1 wherein the sample is blood plasma.

* * * * *

UNITED STATES PATENT AND TRADEMARK OFFICE
CERTIFICATE OF CORRECTION

PATENT NO. : 5,494,797
DATED : February 27, 1996
INVENTOR(S) : Daisy S. McCann et al.

It is certified that error appears in the above-identified patent and that said Letters Patent is hereby corrected as shown below:

Column 7, line 25, delete "Lyme disease by detecting".

Column 7, line 36, delete "Lyme disease" and insert therefor ---the organism---.

Column 7, line 37, after "with" insert ---Lyme disease by detecting---. (1st occurr.)

Column 8, line 25, delete "or" and insert therefor ---of---.

Signed and Sealed this

Sixth Day of August, 1996

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: Linear ( i x ) SEQUENCE DESCRIPTION: SEQ ID NO:1:

```
GTTCGCCTTC  GCCTCCGGTA      20

TTC                         23
```